United States Patent
Behr et al.

(10) Patent No.: US 6,790,987 B2
(45) Date of Patent: Sep. 14, 2004

(54) PROCESS FOR THE CATALYTIC CLEAVAGE OF LACTONES

(75) Inventors: Arno Behr, Dortmund (DE); Volker Brehme, Dortmund (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/362,057

(22) PCT Filed: Aug. 3, 2001

(86) PCT No.: PCT/EP01/09021
§ 371 (c)(1),
(2), (4) Date: Feb. 20, 2003

(87) PCT Pub. No.: WO02/16301
PCT Pub. Date: Feb. 28, 2002

(65) Prior Publication Data
US 2003/0176737 A1 Sep. 18, 2003

(30) Foreign Application Priority Data
Aug. 24, 2000  (DE) .......................... 100 41 571

(51) Int. Cl.⁷ .......................... C07C 51/09; C07C 53/00
(52) U.S. Cl. .................. 562/512; 562/598; 562/606
(58) Field of Search ................. 562/512, 598, 562/606

(56) References Cited

U.S. PATENT DOCUMENTS 3,849,457 A * 11/1974 Haag et al. .................. 560/8
6,291,390 B1  9/2001 Pitter et al. .................. 502/213

OTHER PUBLICATIONS

Z. Chem, 25 (1985), 220–221.
Chemie–Ingenieur Technik (72) 2000, 58–61.

* cited by examiner

Primary Examiner—Ba K. Trinh
(74) Attorney, Agent, or Firm—Keil & Weinkauf

(57) ABSTRACT

The present invention relates to a process of cleaving lactones optionally having functional groups to give carboxylic acids, where the corresponding lactone is reacted with hydrogen with catalysis by a compound of a metal of group VIII of the Periodic Table of the Elements which has been modified with organophosphines. The process is preferably carried out in a two-phase system using catalysts which have water-soluble phosphine ligands.

The reaction is particularly suitable for cleavage 2-ethylidene-6-hepten-5-olide to give ethylidene-6-heptenecarboxylic acid or isomers thereof. This carboxylic acid can be hydrogenated in a manner known per se to give 2-ethylheptanoic acid.

55 Claims, No Drawings

PROCESS FOR THE CATALYTIC CLEAVAGE OF LACTONES

The present invention relates to a catalytic process for the preparation of carboxylic acids by catalytic cleavage of lactones over catalysts derived from metals of group VIII of the Periodic Table of the Elements. In contrast to the known cleavage of lactones by saporification, in which carboxylic acids having hydroxyl groups originating from the lactone group, or functions formed from these form, in the cleavage according to the invention a carboxyl function is formed from the lactone function present in the molecule, although no hydroxyl function or functional group derived therefrom is formed.

Lactones play an important role, for example, in the fragrance and flavor industry. By contrast, as a starting material for the preparation of other products, lactones have hitherto only appeared to a minor degree. This is due, firstly, to the reactivity of the lactones. In the simplest reaction of lactones, hydrolysis, hydroxycarboxylic acids or derivatives thereof are formed. It is generally necessary to reduce the hydroxyl function; firstly to provide carboxylic acids or also esters with a broad potential field of use, and secondly, of course, also to avoid the back-formation of lactone. The otherwise known reactions of lactones virtually always lead only to products which are of no or only low industrial importance and/or can be prepared more favorably by another method.

It is also a factor here that, in addition to the frequently undesired reactivity pattern, lactones are generally expensive products. This is due to the comparatively complex preparation process. Of the processes for lactone preparation, the telomerization of butadiene with $CO_2$ and optionally further starting material compounds has recently become the focal point. As the starting materials are low in cost and present in large amounts, some lactones at least have become accessible at low cost and are available as starting substances for secondary reactions, some of which have still to be developed, to give products which are of potential interest for certain fields of application.

One example of a readily accessible lactone which may be mentioned is the δ-lactone 2-ethylidene-6-heptenolide, which is prepared in a telomerization reaction from two molecules of butadiene and one molecule of $CO_2$. Organophosphine-modified palladium complexes are used as catalysts. The process can be modified in various ways. Using modem process variants, yields of 95% with regard to the lactone are possible, and even the problem of catalyst recycling has meanwhile been solved in a number of ways. According to the process disclosed in WO 98/57745, this is possible, for example, by immobilizing the catalyst on a polystyrene support, or by extracting the resulting lactone when the reaction is complete and returning the catalyst which is insoluble in the extractant. This last process is disclosed in Chemie-Ingenieur-Technik 72 (2000), pages 58 to 61.

Hitherto known secondary reactions which have been carried out on this lactone are alkaline cleavage, which produces, as product, 2-ethylidene-5-hydroxy-6-heptenoic acid, and acid-catalyzed cleavage in the presence of methanol, which produces a mixture of the methoxy derivatives and the methylester of the abovementioned acid, see Z. Chem. 25 (1985), pages 220 to 221. Also known is the synthesis of the corresponding γ-lactone from 2-ethylidene-6-heptenolide.

It is an object of the present invention to provide a process with which lactone cleavages can be carried out which produce, as secondary products, carboxylic acids which do not have hydroxyl groups or substituents derived therefrom. The process should be easy to carry out, produce high yields and leave intact other functional groups present on the lactone, such as, for example, olefin functions.

We have found that this object is achieved by a process for cleaving lactones optionally having functional groups to give carboxylic acids, this process comprising reacting the corresponding lactone with hydrogen under catalysis by a compound of a metal of group VIII of the Periodic Table of the Elements which has been modified with organophosphines.

The process according to the invention permits, as a result of the cleavage of lactones, the preparation of carboxylic acids which no longer have hydroxyl groups originating from the lactone function, but in which other functional groups are generally still present.

This is a transition-metal-catalyzed process in which catalytically active complexes of metals of group VIII of the Periodic Table of the Elements which have been modified with phosphine ligands are used. The metals are preferably chosen from the group consisting of Ru, Os, Pd, Pt, Rh and Ir. In particular, the metals are chosen from the group consisting of Rh and Ir.

The type of phosphine ligands which are used varies depending on the method by which the process according to the invention is carried out. This process can be carried out homogeneously in an organic phase, optionally with the addition of a solvent, heterogeneously in organic phase using an insoluble catalyst fixed to a support, optionally with the addition of an organic solvent, or in a two-phase system having one aqueous phase and one organic phase, optionally with the addition of an organic solvent.

If the homogeneous reaction method is chosen, the customary organophosphines are generally suitable; these may be mono-, bi- or else polydentate. In general, mono- or bidentate phosphines are used. These may be chosen from the known organophosphines soluble in the customary solvents. These are, for example, triarylphosphines, trialkylphosphines and alkylene- and arylene-bridged diphosphines which carry alkyl or aryl substituents. Examples include trimethylphosphine, triisopropylphosphine, tricyclohexylphosphine, triphenylphosphine, diphenylphosphinoethane and -methane, dimethylphosphinoethane and -methane, and the phosphines known under the name BINAP.

If the abovementioned phosphines are used, the reaction is carried out without the addition of a solvent or with the addition of a customary solvent, for example heptane, toluene, diethyl ether, dioxane or methanol or else mixtures thereof.

The resulting carboxylic acid is isolated by, for example, removing it from the reaction mixture by distillation, or extracting it therefrom, for example by acid-base extraction or using a suitable solvent.

Simple isolation and separation of the product from the catalyst is, according to one variant of the present invention, possible using phosphine ligands fixed to supports. All of the abovementioned phosphine ligands suitable for use in the process according to the invention can be fixed to suitable supports. These are, firstly, organic polymers, for example polystyrene, which may optionally be modified (Merrifield resin, Wang resin, aminomethyl-substituted polystyrene), Tentagel and polyamide resins. It is also possible to use inorganic supports, such as silicon dioxide and pulp.

In this process variant in which organophosphines fixed to supports are used, the reaction mixture can, when the reaction is complete, be separated off simply by decantation from the catalyst, which can then be reintroduced into the reaction. The reaction mixture separated off from the catalyst is then isolated and purified using customary methods, for example removal of the solvent by distillation followed by purification of the product by distillation.

In a preferred embodiment of the present invention, the process is carried out in a water/organic solvent two-phase system, in which case water-soluble phosphine ligands are used. These phosphine ligands may be mono- or bidentate and have the customary organic groups known to a person skilled in the art on the organic substituents bonded to the phosphorous, as a result of which the solubility in water is effected. Examples of such groups which effect solubility in water include carboxyl functions, hydroxyl functions, alkoxylated hydroxyl functions, phosphonato functions and sulfonyl functions, preferably sulfonyl functions.

One group of suitable water-soluble phosphine ligands are the triarylphosphines corresponding to the formula (I) below

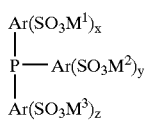
(I)

in which Ar is a phenyl or naphthyl radical, M1, M2 and M3, independently of one another, are an alkali metal ion, an optionally organosubstituted ammonium ion, an alkaline earth metal ion or a zinc ion and are present in the stoichiometrically required amount, and x, y and z are identical or different and independently of one another are 0 or 1.

Preferably, in formula (I), x, y and z are 1, and Ar is a phenyl radical. In particular, trisodium tri(n-sulfonyl) phosphine (TPPTS) is used as ligand according to formula (I).

Another group of suitable substituents corresponds to the formulae (IIa) or (IIb)

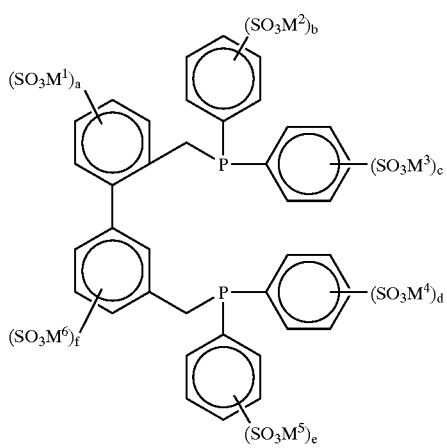
(IIa)

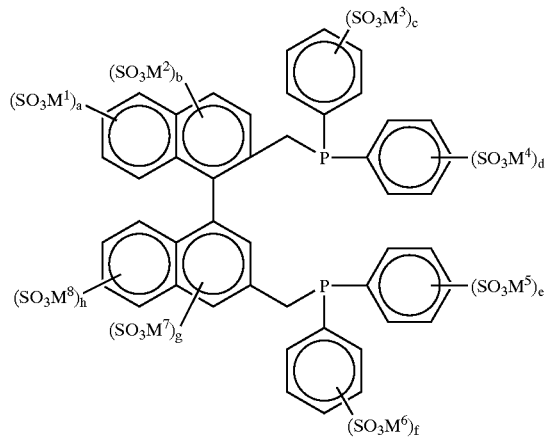
(IIb)

in which M1 to M6 or M1 to M8, respectively, independently of one another are an alkali metal ion, an optionally organosubstituted ammonium ion, an alkaline earth metal ion or a zinc ion, and are present in the stoichiometrically required amounts, and a-f and a-h, respectively, independently of one another are 0 or 1.

Preferred phosphines of the formula (IIa) are those in which 3 to 6 sulfonyl groups $SO_3M$ are present; preferred phosphines according to the formula (IIb) have 4 to 8 sulfonyl groups. Of the phosphines corresponding to the formulae (IIa) and (IIb), particular preference is given to the ligands known under the name BISBIS and BINAS.

If the reaction is carried out in a two-phase system, an organic solvent may be present, but the reaction may also be carried out in the absence of a solvent. Examples of suitable organic solvents include nonpolar solvents, such as paraffins, aromatic solvents, for example toluene and xylene, ethers, such as, for example, diethyl ether and methyl tert-butyl ether, acetonitrile and chlorinated hydrocarbons, such as, for example, dichloromethane and chloroform.

The catalytically active catalyst complex is prepared by generally known methods, generally by mixing a suitable precursor compound with the respective phosphine ligands in the required amounts. Suitable precursor compounds are known to the person skilled in the art. Suitable rhodium precursor compounds include, for example, $RhCl_3.3H_2O$, $[Rh(COD)Cl]_2$ (COD=1,5-cyclooctadiene) and $Rh(CH_3COO)_3$ and other compounds known to the person skilled in the art.

Examples of suitable iridium precursor compounds which may be mentioned are $IrCl_6^{3-}$, $IrCl_3.n\ H_2O$ and $H_2[IrCl_6].n\ H_2O$.

The phosphine ligands used in the process according to the invention are used in all process variants in relative amounts with regard to the rhodium or iridium metal which are at values of from 1:3 to 1:1000, preferably 1:10 to 1:100. The catalyst is used in an amount which is at values of from 100 to 10000, preferably 500 to 10000, mol of lactone/mol of metal ion.

In the preferred process variant according to the present invention, in which the water-soluble phosphines (I), (IIa) or (IIb) are used, the metal/phosphine ligand ratio is 1:3 to 1:1000, preferably 10 to 100. The aqueous phase comprises here 20 to 5000 ppm of metal ion, preferably 250 to 1500 ppm. The relative amount of metal ions which is used is $1 \cdot 10^{-5}$ to $1 \cdot 10^{-2}$ mol of metal ion/mol of lactone. The aqueous phase comprises here 1 to 25% by weight, preferably 2.5 to 15% by weight, of phosphine ligand.

The process according to the invention is carried out in all process variants at temperatures of from 50 to 200° C. If functional groups are present on the lactone, the temperature is preferably 50 to 150° C., in particular 70 to 130° C., and the process is carried out under a hydrogen atmosphere at pressures of from 1 to 150 bar, preferably 1 to 30 bar.

The product mixture obtained following cleavage of the lactone and which has the carboxylic acids formed is separated from the solution which comprises the catalytically active metal complex or the phosphine ligands. In the case of a homogeneous reaction method in the organic phase, this is achieved by distilling off the solvent and distilling the residue containing the product, optionally following oxidation of the phosphine ligands or converting them into a phosphonium salt. If an immobilized ligand is used, the product solution is removed from this by decantation and subsequently worked up in an appropriate manner.

If the process is carried out as a two-phase reaction, the work-up comprises, firstly, simply separating off the organic phase which contains the product from the aqueous phase. The carboxylic acid is then purified by the known methods, conventionally by distillation. The aqueous catalyst solution can then be reused.

The process of lactone cleavage according to the invention can be used widely and is suitable both for $\gamma$-lactone and for $\delta$-lactone. It is possible to use lactones which have different substituents on their ring system or else themselves have a double bond in the ring. Examples of functional groups which can have the lactone substrate include olefinic double bonds and acetylenic triple bonds, carboxyl functions, carbonyl functions, hydroxyl functions, epoxide functions, nitrile groups, amino groups, nitro groups, in particular olefinic double bonds.

Depending on the reaction conditions chosen a double-bond isomerization can be observed. Nonobservance of the respective reaction conditions required for the reaction to proceed gently to attain only the desired lactone cleavage, may also lead to the observance of a more or less complete hydrogenation of the functional groups, such as, for example, of the olefinic double bonds.

As already mentioned, one of the advantages of the process according to the invention is that functional groups are retained during the lactone cleavage. In particular, the process of lactone cleavage according to the invention can be readily carried out such that no olefinic double bonds are hydrogenated. The process is therefore suitable in particular for the cleavage of lactones which have olefinic double bonds on the substituents or an olefinic double bond in the ring itself.

The process of lactone cleavage according to the invention is particularly suitable for converting 2-ethylidene-6-hepten-5-olide into 2-ethylidene-6-heptenoic acid or isomers thereof. Here, it is possible to achieve conversions of 100% and selectivities for the 2-ethylidene-6-heptenoic acid or for double-bond isomers which form as a result of rearrangement reactions of up to 100%.

The present application also refers to a process for the preparation of 2-ethylheptanoic acids by cleavage of 2-ethylidene-6-hepten-5-olide and hydrogenation of the resulting 2-ethylidene-6-heptenecarboxylic acid or isomers thereof. 2-Ethylheptanoic acid is an interesting alternative to 2-ethylhexanoic acid. The latter is used as a starting material for lubricants, plasticizers and alkyd resins. The acid is used here, depending on the intended use, in the form of its esters, metal salts or the acid itself. The acid is frequently also converted to the corresponding alcohol by hydrogenation, which alcohol is esterified with certain carboxylic acids and then used as plasticizer.

However, in view of the preparation aspects, 2-ethylheptanoic acid is advantageous since it can be prepared from two $C_4$ building blocks and one $C_1$ building block (butadiene and $CO_2$ respectively). Due to the uneven number of carbons, this is not the case for 2-ethylhexanoic acid, and recourse has to be made to propene for its preparation. However, propene is a raw material in short supply compared with butadiene, meaning that it is desirable to be able to use the latter as a raw material.

2-Ethylheptanoic acid as a $C_9$ acid is known per se. It has properties which predestine it as replacement for 2-ethylhexanoic acid which has hitherto been used on a large scale. However, despite the number of carbon atoms which is favorable per se, it has not hitherto been possible to prepare 2-ethylheptanoic acid in a manner which is cost-effective and which permits synthesis on an industrial scale.

It was a further object of the present invention to provide a process with which 2-ethylheptanoic acid can be prepared simply, cost-effectively and in high yields. The process should in addition be able to be operated on an industrial scale.

This object is achieved by a process for the preparation of 2-ethylheptanoic acids, which comprises the above-described catalytic cleavage of 2-ethylidene-6-hepten-5-olide to give 2-ethylidene-6-heptenoic acids and isomers thereof and the hydrogenation of this carboxylic acid or of the resulting isomer mixture.

According to one embodiment of the present invention, the lactone cleavage and the hydrogenation of the olefinic double bond can be carried out in a single process step. Here, the catalyst used in the lactone cleavage is chosen and the reaction conditions are adjusted such that the reaction is not complete following cleavage of the lactone ring, but the olefinic double bonds in the substrate are likewise hydrogenated. This hydrogenation can be achieved, in particular, using severe reaction conditions, for example temperatures of >125° C. and pressures of >10 bar. According to another preferred embodiment of the present invention, the hydrogenation is carried out using a customary catalyst system known per se over the ethylidene-heptenecarboxylic acid isomer mixture, formed following lactone cleavage, which has been freed from the catalyst system used.

The hydrogenation is carried out using the suitable catalyst compounds known to a person skilled in the art, it being possible for the hydrogenation to be carried out homogeneously or heterogeneously. The hydrogenation is preferably carried out under heterogeneous conditions. In this heterogeneous method, it is preferred to use, as catalyst, metals chosen from the group consisting of nickel, palladium and platinum. Mixtures of these preferred metals can also be used. The catalyst metals or mixtures thereof can be used without support material. If a support material is used, then it consists of the customary materials known to a person skilled in the art, for example activated carbon, $Al_2O_3$, $SiO_2$, $ZrO_2$ and MgO, preferably activated carbon or $Al_2O_3$.

During the hydrogenation of the ethylidene-heptanecarboxylic acids, it is possible for an organic solvent to be present. Examples of suitable organic solvents include lower alcohols, paraffins, ethers. The reaction can, however, also be carried out in the absence of a solvent. The chosen temperatures are from 0 to 300° C., preferably 40 to 220° C., and the pressures are from 1 to 300 bar, preferably 5 to 15 bar.

In this way, complete hydrogenation of the olefinic double bond of the ethylideneheptenoic acids used can be achieved.

The application is now described in more detail in the examples below.

EXAMPLES

Cleavage of the Lactone Ring

1. Procedure in an Autoclave with V=67 ml

The investigations for the cleavage of the lactone ring were carried out in an autoclave with a volume of 67 ml. The reaction solution consisted of two imiscible phases: the aqueous catalyst phase containing $RhCl_3$ as catalyst metal and TPPTS as ligand. The organic phase consisted either of a nonpolar solvent and the starting material, the δ-lactone, or only of the δ-lactone. The volume of the phases was 15 ml in each case. The reactor was provided with an immersion tube which permitted sampling from the organic phase. The two phases were mixed using a disc stirrer.

The reactor was evacuated prior to the start of the reaction and the reaction solution was sucked in using the resulting vacuum. The mixture was then heated to the reaction temperature with slow stirring, the stirrer was switched off, hydrogen was injected to the desired pressure and the reaction was started by switching on the stirrer.

Samples were taken after 5, 10, 15, 30 and 60 min. Analysis was carried out using a HP® 6890 GC-FID.

The results of the experiments with the 67 ml-autoclave are summarized in Table 1. The initial weights of lactone and water were 15 g in each case, giving a mass ratio of organic phase to aqueous phase of 1:1.

The column "Lactone in mol % after t=5 min" gives the molar percentage of the δ-lactone in the autoclave after a reaction time of 5 minutes. The column "Time t in min at convertion=1" gives the sampling time point at which δ-lactone could no longer be detected in the autoclave.

Example 1.1 (Experiment LC8)

The reaction solution consisting of 15.0 g of δ-lactone, 12.5 g of water, 38 mg of $RhCl_3*3H_2O$ and 2.8 ml of 25% strength TPPTS solution is prepared in a Schlenk vessel.

The reactor is evacuated and the reaction solution is sucked in. The mixture is then heated to 80° C. with slow stirring, the stirrer is switched off, hydrogen is injected to a pressure of 10 bar and the reaction is started by accelerating the stirrer to 1000 $min^{-1}$.

Sampling takes place after 5, 10, 15, 30 and 60 min, one minute being waited in each case after the stirrer has been switched off to allow separation of the phases.

TABLE 2

| | Example 1.1 | | | |
|---|---|---|---|---|
| Time t in min | Lactone in mol % | n (Lactone) in mol | TON | TOF in $h^{-1}$ |
| 0 | 98.55 | 0.10 | 0 | 0 |
| 5 | 69.04 | 0.07 | 204 | 2453 |
| 10 | 47.87 | 0.05 | 351 | 2106 |
| 15 | 19.00 | 0.02 | 551 | 2204 |
| 30 | 6.88 | 0.01 | 635 | 1270 |
| 30 | 0.00 | 0.00 | 683 | 683 |

TON = turnover number
TOF = turnover frequency

Example 1.2 (Experiment LC22)

The reaction solution consisting of 15.0 g of δ-lactone, 12.2 g of water, 39 mg of $RhCl_3*3H_2O$ and 2.8 ml of 25% strength TPPTS solution is prepared in a Schlenk vessel.

The reactor is evacuated and the reaction solution is sucked in. The mixture is then heated to 90° C. with slow stirring, the stirrer is switched off, hydrogen is injected to a

TABLE 1

Hydrogenation of δ-lactone using rhodium/triarylphosphine

| Experiment | Ligand | Rh/lactone ppm | P/Rh in mol/mol | Stirrer speed in rpm | Pressure p of $H_2$ in bar | Lactone in mol % after t = 5 min | Temperature in ° C. | Time t in min at conversion = 1 |
|---|---|---|---|---|---|---|---|---|
| LC4 | TPPTS | 1000 | 10 | 1000 | 30 | 35 | 90 | 15 |
| LC5 | TPPTS | 1000 | 10 | 1000 | 10 | 26 | 90 | 60 |
| LC6 | TPPTS | 1000 | 10 | 1000 | 20 | 18 | 90 | 15 |
| LC7 | TPPTS | 1000 | 10 | 1000 | 10 | 56 | 90 | 30 |
| LC8 | TPPTS | 1000 | 10 | 1000 | 10 | 69 | 80 | 60 |
| LC9 | TPPTS | 1000 | 10 | 1000 | 10 | 28 | 100 | 15 |
| LC10 | TPPTS | 1000 | 10 | 1000 | 20 | 45 | 90 | 15 |
| LC12 | TPPTS | 500 | 10 | 1000 | 10 | 44 | 90 | 15 |
| LC13 | TPPTS | 1500 | 10 | 1000 | 10 | 15 | 90 | 30 |
| LC14 | TPPTS | 250 | 10 | 1000 | 10 | 80 | 90 | 60 |
| LC15 | TPPTS | 1500 | 10 | 1000 | 10 | 18 | 90 | 10 |
| LC16 | TPPTS | 500 | 10 | 1000 | 10 | 42 | 90 | 30 |
| LC17 | TPPTS | 1000 | 10 | 1000 | 10 | 63 | 90 | 30 |
| LC18 | TPPTS | 1000 | 10 | 1000 | 10 | 60 | 90 | 15 |
| LC19 | TPPTS | 1000 | 10 | 800 | 10 | 56 | 90 | 30 |
| LC20 | TPPTS | 1000 | 10 | 1200 | 10 | 25 | 90 | 15 |
| LC21 | TPPTS | 1000 | 5 | 1000 | 10 | 63 | 90 | 60 |
| LC22 | TPPTS | 1000 | 10 | 1200 | 10 | 24 | 90 | 15 |
| LC23 | TPPTS | 1000 | 20 | 1000 | 10 | 31 | 90 | 15 |
| LC24 | TPPTS | 1000 | 10 | 600 | 10 | 60 | 90 | 30 |
| LC25 | TPPTS | 500 | 10 | 1000 | 10 | 44 | 90 | 15 |
| LC26 | BINAS | 500 | 10 | 1000 | 10 | 64 | 90 | 60 |
| LC27 | BISBIS | 500 | 10 | 1000 | 10 | 77 | 90 | 60 |

Some of the experiments summarized in the table are described in more detail below by way of example.

pressure of 10 bar and the reaction is started by accelerating the stirrer to 1200 $min^{-1}$.

Sampling takes place after 5, 10, 15 and 30 min, one minute being waited in each case after the stirrer has been switched off to allow separation of the phases.

TABLE 3

Example 1.2

| Time t in min | Lactone in mol % | n (Lactone) in mol | TON | TOF in h$^{-1}$ |
|---|---|---|---|---|
| 0 | 100.00 | 0.10 | 0 | 0 |
| 5 | 23.89 | 0.02 | 530 | 6363 |
| 10 | 5.53 | 0.01 | 658 | 3947 |
| 15 | 0.00 | 0 | 696 | 2785 |
| 30 | 0.00 | 0 | 696 | 1393 |

Example 1.3 (Experiment LC4)

The reaction solution consisting of 15.0 g of δ-lactone, 12.2 g of water, 39 mg of RhCl$_3$*3H$_2$O and 2.8 ml of 25% strength TPPTS solution is prepared in a Schlenk vessel.

The reactor is evacuated and the reaction solution is sucked in. The mixture is then heated to 90° C. with slow stirring, the stirrer is switched off, hydrogen is injected to a pressure of 30 bar and the reaction is started by accelerating the stirrer to 1000 min$^{-1}$.

Sampling takes place after 5, 10 and 15 min, one minute being waited in each case after the stirrer has been switched off to allow separation of the phases.

TABLE 4

Example 1.3

| Time t In min | Lactone in mol % | n (Lactone) in mol | TON | TOF in h$^{-1}$ |
|---|---|---|---|---|
| 0 | 96.82 | 0.10 | 0 | 0 |
| 5 | 34.82 | 0.03 | 431 | 5173 |
| 10 | 6.79 | 0.01 | 626 | 3756 |
| 15 | 0.00 | 0.00 | 673 | 2693 |

Example 1.4 (Experiment LC12)

The reaction solution consisting of 15.0 g of δ-lactone, 13.6 g of water, 19 mg of RhCl$_3$*3H$_2$O and 1.4 ml of 25% strength TPPTS solution is prepared in a Schlenk vessel.

The reactor is evacuated and the reaction solution is sucked in. The mixture is then heated to 90° C. with slow stirring, the stirrer is switched off, hydrogen is injected to a pressure of 10 bar and the reaction is started by accelerating the stirrer to 1000 min$^{-1}$.

Sampling takes place after 5, 10 and 15 min, one minute being waited in each case after the stirrer has been switched off to allow separation of the phases.

TABLE 5

Example 1.4

| Time t in min | Lactone in mol % | n (Lactone) in mol | TON | TOF in h$^{-1}$ |
|---|---|---|---|---|
| 0 | 96.80 | 0.10 | 0 | 0 |
| 5 | 44.02 | 0.04 | 732 | 8784 |
| 10 | 10.92 | 0.01 | 1191 | 7147 |
| 15 | 0.00 | 0.00 | 1343 | 5370 |

Example 1.5 (Not Listed in Table 1)

The reaction solution consisting of 5.0 g of δ-lactone, 6.8 g of n-heptane, 14.06 g of water, 13 mg of RhCl$_3$*3H$_2$O and 1.1 ml of 25% strength TPPTS solution is prepared in a Schlenk vessel.

The reactor is evacuated and the reaction solution is sucked in. The mixture is then heated to 90° C. with slow stirring, the stirrer is switched off, hydrogen is injected to a pressure of 10 bar and the reaction is started by accelerating the stirrer to 1000 min$^{-1}$.

After 60 min, the stirrer is switched off, the phases are separated and the organic phase is analyzed. The δ-lactone was cleaved completely into the unsaturated 2-ethylideneheptenoic acids.

Example 1.6 (Not Listed in Table 1)

The reaction solution consisting of 5.0 g of δ-lactone, 15 g of toluene, 13.3 g of water, 0.24 mg of [Rh(COD)Cl]$_2$ and 1.7 ml of 25% strength TPPTS solution is prepared in a Schlenk vessel.

The reactor is evacuated and the reaction solution is sucked in. The mixture is then heated to 70° C. with slow stirring, the stirrer is switched off, hydrogen is injected to a pressure of 30 bar and the reaction is started by accelerating the stirrer to 1000 min$^{-1}$.

After 3.5 h, 95% conversion of the δ-lactone is observed, which were converted exclusively to the isomeric 2-ethylideneheptenoic acids.

2 Procedure in an Autoclave with V=300 ml

Example 2.1

Adiabatic Reaction Method with Recycling of the Catalyst Solution

The reaction solution consisting of 75.0 g of δ-lactone, 60.8 g of water, 188 mg of RhCl$_3$*3H$_2$O (1000 ppm) and 16.6 ml of 25% strength TPPTS solution is prepared in a Schlenk vessel.

The 300 ml reactor is evacuated and the reaction solution is sucked in. The mixture is then heated to 90° C. with slow stirring, the stirrer is switched off, hydrogen is injected to a pressure of 10 bar and the reaction is started by accelerating the stirrer to 1000 min$^{-1}$.

Sampling takes place after 5, 10, 15, 20 and 25 min, one minute being waited in each case after the stirrer has been switched off in order to permit separation of the phases. After 30 min, the hydrogen is released and the reaction solution is transferred by means of a stream of argon into a separating funnel purged with argon. The phases are separated, and the organic phase is analyzed by means of gas chromatography. The water content of the organic phase is determined by titration. The emptied reactor is evacuated, and the aqueous catalyst phase used is sucked in again. 75.1 g of δ-lactone are introduced into a Schlenk vessel purged with argon and sucked to the catalyst in the reactor. The catalyst phase is used a total of five times. A mixture of isomeric 2-ethylideneheptenoic acids forms, partial hydrogenation of the olefinic double bonds also being observed.

TABLE 6

Example 2.1

| Use of catalyst phase | Initial weight of δ-lactone in g | δ-Lactone conversion in % | Water content of the organic phase in % | Max. temperature in ° C. |
|---|---|---|---|---|
| 1 | 75.0 | 92 | 0.8 | 96 |
| 2 | 75.1 | 100 | 0.6 | 122 |
| 3 | 75.1 | 100 | 0.8 | 131 |
| 4 | 75.2 | 100 | 0.8 | 122 |
| 5 | 75.2 | 100 | 1.0 | 119 |

Example 2.2
Isothermal Method with Recycling of the Catalyst Solution

The reaction was carried out as described in Example 2.1, the reactor being provided with a U-tube, through which cooling water is passed in order to dissipate the heat of reaction liberated.

The reaction solution consisting of 75.0 g of δ-lactone, 60.8 g of water, 94 mg of RhCl$_3$*3H$_2$O (500 ppm) and 16.6 mg of 25% strength TPPTS solution is prepared in a Schlenk vessel.

The reactor is evacuated and the reaction solution is sucked in. The mixture is then heated to 110° C. with slow stirring, the stirrer is switched off, hydrogen is injected to a pressure of 10 bar and the reaction is started by accelerating the stirrer to 1000 min$^{-1}$. After 30 min, the hydrogen is released and the reaction solution is transferred by means of a stream of argon into a separating funnel purged with argon. The phases are separated and the organic phase is analyzed by means of gas chromatography. The water content of the organic phase is determined by titration. The emptied reactor is evacuated and the aqueous catalyst phase used is sucked in again. 75.1 g of δ-lactone are introduced into a Schlenk vessel purged with argon and sucked to the catalyst in the reactor. A total of six experiments are carried out using the same catalyst phase. Deactivation, like hydrogenation of the olefinic double bonds, is not observed.

TABLE 7

| | Example 2.2 | | | |
|---|---|---|---|---|
| Experiment No. | Initial weight of δ-lactone in g | δ-Lactone conversion in % | Water content in % | Max. temperature in ° C. |
| 1 | 75.4 | 78 | 2.2 | 110 ± 2 |
| 2 | 75.1 | 100 | 0.74 | 110 ± 2 |
| 3 | 75.0 | 100 | 0.67 | 110 ± 2 |
| 4 | 75.2 | 100 | 0.66 | 110 ± 2 |
| 5 | 75.5 | 100 | 0.81 | 110 ± 2 |
| 6 | 75.1 | 100 | 0.96 | 110 ± 2 |

Purification of the 2-Ethylideneheptenoic Acid

The isomeric 2-ethylideneheptenoic acids accessible by cleavage of δ-lactone are distilled in order to remove traces of water which remain in the product. At a pressure of p=2*10$^{-2}$ mbar and a temperature of 30° C., the water is removed, and as the temperature of the bath is increased to 110° C. (head temperature 75° C.), the product is obtained as distillate.

Hydrogenation of the 2-Ethylideneheptenoic Acid

The remaining olefinic double bonds of 2-ethylideneheptenoic acid are hydrogenated using a heterogeneous hydrogenation catalyst.

Example 4.1

0.5 g of palladium on activated carbon (5% Pd) is weighed into a 300 ml autoclave. The reaction solution consisting of 10.0 g of 2-ethylideneheptenoic acid and 90 ml of methanol is prepared under argon and sucked into the autoclave which has been evacuated beforehand. The mixture is then heated to 60° C., hydrogen is injected to a pressure of 10 bar and the reaction is started by accelerating the stirrer is 700 min$^{-1}$. After a reaction time of five minutes, the starting material is completely consumed, 2-ethylheptanoic acid forming as the sole product.

Example 4.2

The process is carried out as described in Example 4.1 using 90 ml of n-heptane instead of the methanol. After 30 min, the yield is 100% 2-ethylheptanoic acid.

Example 4.3

The process is carried out as described in Example 4.1 using 10 g of Al$_2$O$_3$ balls (2–4 mm) containing 0.5% palladium as catalyst. After 60 min, the yield is 100% 2-ethylheptanoic acid.

Example 4.4

The process is carried out as described in Example 4.3, using 5 g of palladium on activated carbon granules (1 mm) containing 1% palladium as catalyst. After 30 min, the conversion is 95%, 2-ethylheptanoic acid being formed exclusively.

Example 4.5

0.5 g of palladium on activated carbon (5% Pd) is weighed into a 300 ml autoclave. 68.8 g of 2-ethylidencheptenoic acid are sucked into the autoclave which has been evacuated beforehand. The mixture is then heated to 60° C., hydrogen is injected to a pressure of 30 bar and the reaction is started by accelerating the stirrer to 1000 rpm. After 6 hours, the conversion is 86%, 2-ethylheptanoic acid being formed exclusively.

Example 4.6

2.5 g of palladium on activated carbon (5% Pd) is weighed into a 300 ml autoclave. 50 g of 2-ethylideneheptenoic acid are sucked into the autoclave which has been evacuated beforehand. The mixture is then heated to 190° C., hydrogen is injected to a pressure of 15 bar and the reaction is started by accelerating the stirrer to 700 min$^{-1}$. After 90 min, the conversion is 80%, 2-ethylheptanoic acid being formed exclusively.

We claim:

1. A process for the cleavage of lactones optionally having functional groups to give carboxylic acids, which comprises reacting the corresponding lactone with hydrogen under catalysis by a compound of a metal of group VIII of the Periodic Table of the Elements, wherein the process is carried out homogeneously and optionally with the addition of a solvent, heterogeneously in the organic phase using an insoluble catalyst fixed to a support comprising a phosphine which is fixed to the support and optionally with the addition of an organic solvent, or in a two-phase system with one aqueous phase and one organic phase and optionally with the addition of an organic solvent.

2. A process as claimed in claim 1, wherein the metal is selected from the group consisting of Ru, Os, Pd, Pt, Rh and Ir.

3. A process as claimed in claim 1, wherein the metal compound is a rhodium or iridium compound which has been modified with organophosphines.

4. A process as claimed in claim 1, wherein the process is carried out homogeneously and optionally with the addition of a solvent.

5. A process as claimed in claim 1, wherein the process is carried out heterogeneously in the organic phase using an insoluble catalyst fixed to a support comprising a phosphine which is fixed to the support and optionally with the addition of an organic solvent.

6. A process as claimed in claim 1, wherein the process is carried out in a two-phase system with one aqueous phase and one organic phase and optionally with the addition of an organic solvent.

7. A process as claimed in claim 4, wherein the process is carried out in the organic phase and mono- or bidentate phosphines are used.

8. A process as claimed in claim 7, wherein trialkylphosphines, triarylphosphines, alkylene- or arylene-bridged diphosphines having alkyl or aryl substituents are used.

9. A process as claimed in claim 7, wherein trimethylphosphine, triisopropylphosphine, tricyclohexylphosphine, triphenylphosphine, diphenylphosphinoethane, diphenylphosphinomethane, dimethylphosphinoethane, dimethylphosphinoethane or BINAP are used.

10. A process as claimed in claim 5, wherein the phosphine is fixed to an organic support.

11. A process as claimed in claim 10, wherein the organic support is optionally modified polystyrene, Merrifield resin, Wang resin, aminomethyl-substituted polystyrene, Tentagel or polyamide resins.

12. A process as claimed in claim 5, wherein the phosphine is fixed to an inorganic support.

13. A process as claimed in claim 12, wherein the inorganic support is silicon dioxide or pulp.

14. A process as claimed in claim 5, wherein the reaction is carried out in a two-phase system having an aqueous phase and an organic phase using a mono- or bidentate water-soluble phosphine.

15. A process as claimed in claim 14, wherein the phosphine is a phosphine which has at least one carboxyl function, hydroxyl function, alkoxylated hydroxyl function, phosphonato function or sulfonyl function.

16. A process as claimed in claim 14, wherein the phosphine is a phosphine having at least one sulfonyl group.

17. A process as claimed in claim 14, wherein the phosphine is selected from triarylphosphines of the formula (I)

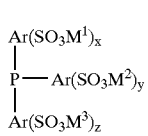

(I)

in which

Ar is phenyl or naphthyl radical, $M^1$, $M^2$ and $M^3$, independently of one another, are an alkali metal ion, an optionally organo-substituted ammonium ion, an alkaline earth metal ion or a zinc ion and are present in the stoichiometrically required amount, and x, y and z are identical or different and independently of one another are 0 or 1.

18. A process as claimed in claim 14, wherein the phosphine is selected from phospine of the formula (IIa)

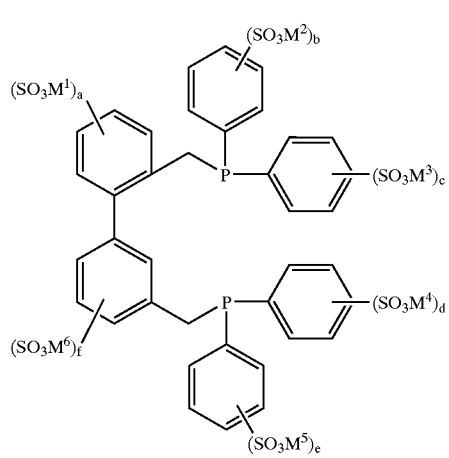

(IIa)

in which $M^1$ to $M^6$ independently of one another are an alkali metal ion, an optionally organo-substituted ammonium ion, an alkaline earth metal ion or a zinc ion and are present in the stoichiometrically required amounts, and a-f independently of one another are 0 or 1.

19. A process as claimed in claim 18, wherein the phosphine has 3 to 6 sulfonyl groups.

20. A process as claimed in claim 14, wherein the phosphine is selected from phosphines of the formula (IIb)

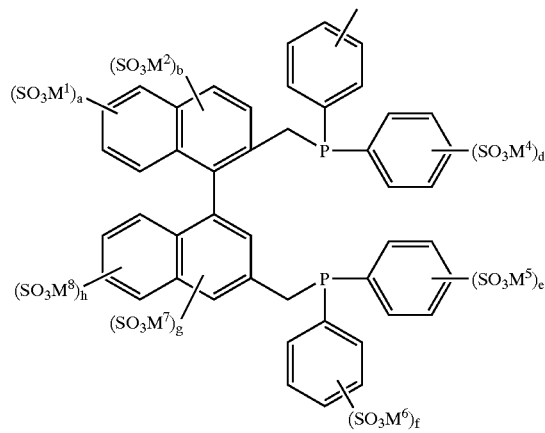

(IIb)

in which $M^1$ to $M^8$ independently of one another are an alkali metal ion, an optionally organo-substituted ammonium ion, an alkaline earth metal ion or a zinc ion and are present in the stoichiometrically required amounts, and a–h independently of one another are 0 or 1.

21. A process as claimed in claim 20, wherein the phosphine has 4 to 8 sulfonyl groups.

22. A process as claimed in claim 14, wherein a phosphine is used which is chosen from the group consisting of the phosphines known under the names TPPTS, BISBIS and BISNAS.

23. A process as claimed in claim 1, wherein the catalytically active complex is prepared by mixing a suitable precursor compound with the corresponding phosphine ligands in the required amounts.

24. A process as claimed in claim 23, wherein the precurser compound is selected from $RhCl_3.3H_2O$, $[Rh(COD)Cl]_2$, or $Rh(CH_3COO)_3$ and $IrCl_6^{3-}$, $IrCl_3. nH_2O$ or $H_2[IrCl_6].nH_2O$.

25. A process as claimed in claim 7, wherein the phosphine ligands are used, with regard to the rhodium and iridium metal, in relative amounts of from 1:3 to 1:1000 and the catalyst is used in an amount of from 100 to 10,000 mol of lactone/mol of metal ion.

26. A process as claimed in claim 25, wherein the relative amount of the phosphine ligand is 10 to 100.

27. A process as claimed in claim 25, wherein the catalyst amount is from 500 to 10,000 mol.

28. A process as claimed in claim 10, wherein the phosphine ligands are used, with regard to the rhodium and iridium metal, in relative amounts of from 1:3 to 1:1000 and the catalyst is used in an amount of from 100 to 10,000 mol of lactone/mol of metal ion.

29. A process claimed in claim 28, wherein the relative amount of the phosphine ligand is 10 to 100.

30. A process as claimed in claim 28, wherein the catalyst amount is from 500 to 10,000 mol.

31. A process as claimed in claim 14, wherein the phosphine ligands are used, with regard to the rhodium and iridium metal, in relative amounts of from 1:3 to 1:1000 and the catalyst is used in an amount of from 100 to 10,000 mol of lactone/mol of metal ion.

32. A process as claimed in claim 31, wherein a phosphine corresponding to one of the formulate (I), (IIa) or (IIb) is used and the metal/phosphine ligand ratio is 1:3 to 1:1000, and the aqueous phase comprises 20 to 1000 ppm of metal ion.

33. A process as claimed in claim 32, wherein the ratio is 10 to 100.

34. A process as claimed in claim 32, wherein the amount of metal ion is 250 to 1500 ppm.

35. A process as claimed in claim 32, wherein the relative amount of metal ions used is $2 \cdot 10^{-6}$ to $5 \cdot 10^{-2}$ mol of metal ions/mol of lactone, and the aqueous phase comprises 1 to 25% by weight of phosphine ligand.

36. A process as claimed in claim 35, wherein the amount of phosphine ligand is 2.5 to 15% by weight.

37. A process as claimed in claim 1, wherein the process is carried out at temperatures of from 50 to 200° C. and at hydrogen pressures of from 1 to 150 bar.

38. A process as claimed in claim 37, wherein the process is carried out at a temperature from 50 to 150° C.

39. A process as claimed in claim 37, wherein the process is carried out at a temperature from 70 to 130° C.

40. A process as claimed in claim 37, wherein the process is carried out at a temperature pressure of from 1 to 30 bar.

41. A process as claimed in claim 1, wherein the lactone is chosen from the group consisting of γ- and δ-lactones which optionally have functional groups or a double bond in the ring.

42. A process as claimed in claim 41, wherein the functional group is an olefinic double bond.

43. A process as claimed in claim 42, wherein the lactone used is 2-ethylidene-6-hepten-5-olide.

44. A process as claimed in claim 43, wherein 2-ethylidene-6-heptenoic acid or one or more isomers of this acid form.

45. A process for the preparation of 2-ethylheptanoic acid, which comprises cleavage and hydrogenation of 2-ethylidene-6-hepten-5-olide by the process as claimed in claim 1 to give 2-ethylidene-6-heptenoic acid and/or one or more isomers thereof.

46. A process as claimed in claim 45, wherein the ring cleavage and the hydrogenation are carried out in one process step.

47. A process as claimed in claim 45, wherein the hydrogenation is carried out following cleavage of the lactone and isolation of the resulting product from the catalyst solution used therein in a manner known per se in a homogeneously or heterogeneously catalyzed reaction method.

48. A process as claimed in claim 47, wherein the hydrogenation is carried out heterogeneously over catalysts chosen from the group consisting of nickel, palladium and platinum and mixtures of these metals.

49. A process as claimed in claim 47, wherein the catalyst is used without support material.

50. A process as claimed in claim 49, wherein the catalyst is applied to a support material chosen from the group consisting of activated carbon, $Al_2O_3$, $SiO_2$, $ZrO_2$ and MgO.

51. A process as claimed in claim 50, wherein the support is selected from activated carbon or $Al_2O_3$.

52. A process as claimed in claim 45, wherein the reaction is carried out at a temperature of from 0 to 300° C. and a pressure from 1 to 300 bar.

53. A process as claimed in claim 52, wherein the temperature is from 40 to 220° C.

54. A process as claimed in claim 53, wherein the pressure is from 5 to 15 bar.

55. A process as claimed in claim 17, wherein Ar is phenyl.

* * * * *